United States Patent [19]

Hunt et al.

[11] Patent Number: 4,911,754

[45] Date of Patent: Mar. 27, 1990

[54] HERBICIDALLY ACTIVE ARYLOXY SATURATED 5-MEMBERED BENZO FUSED HETERO-CYCLIC COMPOUNDS

[75] Inventors: David A. Hunt, Copley; James A. Schwindeman, Akron, both of Ohio

[73] Assignee: American Cyanamid Company, Stamford, Conn.

[21] Appl. No.: 74,106

[22] Filed: Jul. 16, 1987

[51] Int. Cl.$^4$ .................. A01N 37/24; C07D 209/08; C07D 209/12; C07D 209/14

[52] U.S. Cl. ............................................. 71/96; 71/86; 71/87; 71/88; 71/90; 71/91; 71/92; 71/94; 71/95; 71/98; 71/103; 71/105; 71/106; 71/123; 546/22; 546/269; 546/270; 546/271; 546/272; 546/273; 546/274; 548/122; 548/123; 548/124; 548/152; 548/217; 548/221; 548/300; 548/469; 548/470; 548/486; 568/12; 568/27; 568/28; 568/635; 568/639

[58] Field of Search ............................ 71/96; 548/486

[56] References Cited

U.S. PATENT DOCUMENTS

| | | | |
|---|---|---|---|
| Re. 32,316 | 12/1986 | Theissen | 71/96 X |
| 4,288,243 | 9/1981 | Grove | 71/96 X |
| 4,377,408 | 3/1983 | Steffens | 71/92 |
| 4,427,441 | 1/1984 | Wu et al. | 71/96 |
| 4,500,341 | 2/1985 | Forster et al. | 71/96 X |
| 4,619,689 | 10/1986 | Yoshimoto et al. | 71/96 X |
| 4,808,750 | 2/1989 | Rogers et al. | 558/390 X |

FOREIGN PATENT DOCUMENTS

| | | |
|---|---|---|
| 0008226 | 2/1980 | European Pat. Off. |
| 0255178 | 2/1988 | European Pat. Off. |

*Primary Examiner*—Joseph Paul Brust
*Attorney, Agent, or Firm*—Alice C. Brennan

[57] ABSTRACT

This invention relates to aryloxy dihydrobenzofuran, oxoindole or benzofuranone derivatives having herbicidal activity and to the use of such compounds to control the growth of noxious plants, i.e., weeds.

4 Claims, No Drawings

HERBICIDALLY ACTIVE ARYLOXY SATURATED 5-MEMBERED BENZO FUSED HETERO-CYCLIC COMPOUNDS

FIELD OF THE INVENTION

This invention relates to aryloxy dihydrobenzofuran, oxoindole or benzofuranone derivatives having herbicidal activity and to the use of such compounds to control the growth of noxious plants, i.e., weeds.

DESCRIPTION OF THE INVENTION

This invention provides herbicidally active aryloxy dihydrobenzofuran, oxoindole or benzofuranone compounds represented by the Formula I:

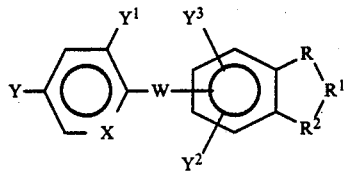

wherein:
W is O or $S(O)_x$ wherein x is 0, 1 or 2;
X is N or $CY^4$ wherein $Y^4$ is hydrogen, halogen, cyano, nitro or $C_1$ to $C_4$ haloalkyl;
Y and $Y^1$ are independently hydrogen, halogen, cyano, nitro or $C_1$ to $C_4$ haloalkyl;
$Y^2$ and $Y^3$ are independently hydrogen, halogen, cyano, nitro or $C_1$ to $C_6$ alkyl, haloalkyl, alkoxy, alkoxyalkyl or carboalkoxy;
R, $R^1$ and $R^2$ are independently N or NZ wherein Z is hydrogen or $C_1$ to $C_4$ alkyl; O, CO, $S(O)_x$ or $CS(O)_x$ wherein x is 0, 1 or 2; $PZ^1$ or $P(O)Z^1$ wherein $Z^1$ is $C_1$ to $C_6$ alkyl; $CZ^2Z^3$ wherein $Z^2$ is hydrogen or $C_1$ to $C_6$ alkyl and $Z^3$ is hydrogen or up to $C_6$ alkyl, alkoxy, alkoxyalkyl, aminoalkyl, hydroxyalkyl, alkenyl or alkynyl; or $CNOZ^4$ wherein $Z^4$ is hydrogen or up to $C_6$ alkyl, alkenyl, alkynyl, carboxy or carboalkoxyalkyl; with the proviso that R, $R^1$ and $R^2$ cannot all be the same.

Preferred compounds of the Formula I are those wherein Y is trifluoromethyl; $Y^1$ is halogen, especially chlorine or fluorine; X is $CY^4$ wherein $Y^4$ is hydrogen or halogen, especially chlorine or fluorine; $Y^2$ and $Y^3$ are each hydrogen; W is O; R is O, N or NZ wherein Z is hydrogen or $C_1$ to $C_4$ alkyl; $R^1$ is CO, N or NZ wherein Z is $C_1$ to $C_4$ alkyl; and $R^2$ is $CZ^2Z^3$ wherein $Z^2$ and $Z^3$ are hydrogen or $C_1$ to $C_4$ alkyl.

Particularly preferred compounds are those wherein R is NZ wherein Z is hydrogen or $C_1$ to $C_4$ alkyl; $R^1$ is CO; and $R^2$ is $CZ^2Z^3$ wherein $Z^2$ and $Z^3$ are hydrogen or $C_1$ to $C_4$ alkyl.

The compounds of this invention may be readily synthesized using methods known to the art. For example, a suitably substituted benzene or pyridine of the Formula II:

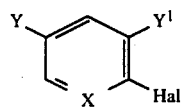

wherein Y, $Y^1$ and X are as previously defined and Hal is halogen, preferably chlorine, bromine or fluorine, is reacted with a suitably substituted compound of the formula III:

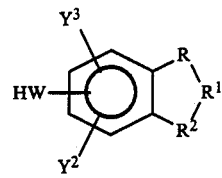

where W, $Y^2$, $Y^3$, R, $R^1$ and $R^2$ are as previously defined to form a compound of the Formula I.

The following Examples are illustrative of the preparation of certain compounds of the invention.

EXAMPLE I

Preparation of:
2-methyl-5-(5-trifluoromethyl-2-pyridyloxy)-2,3-dihydrobenzofuran A stirred mixture of 2.18 grams (0.012 mole) of 2-chloro-5-trifluoromethyl pyridine, 1.80 grams (0.012 mole) of 2,3-dihydro-2-methyl benzofuranol, 2.07 grams (0.015 mole) of potassium carbonate and 80 milliliters of dimethylsulfoxide was heated, under anhydrous conditions, at a temperature in the range of 65°–72° C. for about 72 hours. After heating was discontinued, the mixture was stirred overnight, then poured into 800 milliliters of water and extracted with 2×250 milliliter portions of diethylether. The combined organic extracts were washed with 2×300 milliliter portions of water, dried over anhydrous magnesium sulfate, filtered and concentrated in vacuo affording 2.60 grams of brown oil. The crude product was purified by column chromatography and eluted with 5:95 v/v ethyl acetate:hexane affording 1.64 grams of white crystals confirmed by spectroscopic analysis as the desired product.

EXAMPLE II

Preparation of:
2-ethoxy-3,3-dimethyl-5-(2-chloro-4-trifluoromethyl-6-fluorophenoxy)-2,3-dihydrobenzofuran A stirred mixture of 1.19 grams (0.00551 mole) of 3-chloro-4,5-difluorobenzotrifluoride, 1.15 grams (0.00551 mole) of 2-ethoxy-3,3-dimethyl-2,3-dihydrobenzofuranol, 0.91 gram (0.00661 mole) of potassium carbonate and 50 milliliters of acetonitrile was heated to reflux and refluxed for about 18 hours under anhydrous conditions. After cooling to room temperature, the reaction mixture was poured into 100 milliliters of water and extracted with 2×75 milliliter portions of chloroform. The combined organic extracts were dried over anhydrous magnesium sulfate, filtered and concentrated in vacuo affording 1.90 grams of pale brown oil confirmed by spectroscopic analysis as the desired product.

EXAMPLE III

Preparation of
5-(2-chloro-4-trifluoromethyl-6-fluorophenoxy)-1,3,3-trimethyl-2-oxoindole A stirred mixture of 0.33 gram (0.0015 mole) of 3-chloro-4,5-difluorobenzotrifluoride, 0.29 gram of 5-hydroxy-1,3,3-trimethyl-2-oxoindole, 0.41 gram (0.003 mole) of potassium carbonate and 50 milliliters of acetonitrile was heated to relfux and refluxed for about 18 hours under anhydrous conditions. After cooling, the reaction mixture was filtered and concentrated in vacuo affording 0.5 gram of brown gum confirmed by spectroscopic analysis as the desired product.

EXAMPLE IV

Preparation of: 5-(2-chloro-4-trifluoromethylphenoxy)-1,3,3-trimethyl-2-oxoindole A stirred mixture of 1.99 grams (0.01 mole) of 3-chloro-4-fluorobenzotrifluoride, 1.91 grams (0.01 mole) of 5-hydroxy-1,3,3-trimethyl-2-oxoindole, 2.07 grams (0.015 mole) of potassium carbonate and 125 milliliters of acetonitrile was heated to reflux and refluxed under anhydrous conditions for about 2 days. After cooling the reaction mixture was filtered and concentrated in vacuo affording a tan solid. Since LC analysis indicated the presence of unreacted starting material, the crude material was dissolved in 200 milliliters of methylene chloride and washed with 100 milliliter of 5 percent aqueous sodium hydroxide. Drying over magnesium sulfate, filtration and concentration in vacuo afforded 2.12 grams of an off-white granular solid confirmed by spectroscopic analysis as the desired product.

EXAMPLE V

Preparation of 5 (2-chloro-4-trifluoromethyl-6-fluorophenoxy)-1,3-dimethyl-3-ethyl-2-oxoindole A stirred mixture of 0.76 gram (0.00371 mole) of 1,3-dimethyl-3-ethyl-5-hydroxy-2-oxoindole, 0.80 gram (0.00371 mole) of 3-chloro-4,5-difluorobenzotrifluoride, 0.77 gram (0.00556 mole) of potassium carbonate and 125 milliliters of acetonitrile was heated to reflux and maintained at reflux, under anhydrous conditions, for about 24 hours. The reaction mixture was then cooled, filtered and concentrated in vacuo affording 1.25 grams of brown syrup confirmed by spectroscopic analysis as the desired product.

VII The compound: 2-methyl-5-(2-chloro-4-trifluoromethylphenoxy)-2,3-dihydrobenzofuran.

VIII The compound: 2-methyl-5-(2-chloro-4-trifluoromethyl-6-fluorophenoxy)-2,3-dihydrobenzofuran.

IX The compound: 2-ethoxy-3,3-dimethyl-5-(5-trifluoromethylpyridyloxy)-2,3-dihydrobenzofuran.

X The compound: 2-ethoxy-3,3-dimethyl-5-(3-chloro-5-trifluoromethyl-2-pyridyloxy)-2,3-dihydrobenzofuran.

XI The compound: 2-methyl-5-(3-chloro-5-trifluoromethylpyridyloxy)-2,3-dihydrobenzofuran.

XII The compound: 4-(5-trifluoromethyl-pyridyloxy)-1,2-methylenedioxybenzene

XIII The compound: 5-(5-trifluoromethyl-2-pyridyloxy)-1,3,3-trimethyl-2-oxoindole XIV The compound: 5-(2-chloro-4-trifluoromethyl-6-fluorophenoxy)-2-oxoindole.

XV The compound: 5-(5-trifluoromethyl-2-pyridyloxy)-1,3-dimethyl-3-ethyl-2-oxoindole.

XVI The compound: 5-(5-trifluoromethyl-2-pyridyloxy)-2-ethyl-3,3-dimethyl-2-oxoindole.

XVII The compound: 5-(2-chloro-4-trifluoromethyl-6-fluorophenoxy)-1-ethyl-3,3-dimethyl-2-oxoindole.

XVIII The compound: 2-carbomethoxy-5-(2-chloro-4-trifluoromethyl-6-fluorophenoxy)-benzofuran-3,(2H)-one.

The compounds prepared according to the following Examples I to XX are represented by the following general Formula IV:

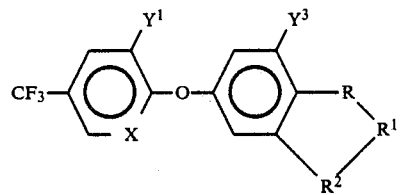

wherein X, $Y^1$, $Y^3$, R, $R^1$ and $R^2$ are as follows:

| Example | X | $Y^1$ | $Y^3$ | R | $R^1$ | $R^2$ |
|---------|---|-------|-------|---|-------|-------|
| I | N | H | H | O | CH—CH$_3$ | CH$_2$ |
| II | C—F | Cl | H | O | CH—OCH$_2$CH$_3$ | C(CH$_3$)$_2$ |
| III | C—F | Cl | H | N—CH$_3$ | C=O | C(CH$_3$)$_2$ |
| IV | C—H | Cl | H | N—CH$_3$ | C=O | C(CH$_3$)$_2$ |
| V | C—F | Cl | H | N—CH$_3$ | C=O | C(CH$_3$)(CH$_2$CH$_3$) |
| VI | C—H | Cl | COOCH$_3$ | O | CH—CH$_2$OH | CH$_2$ |
| VII | C—H | Cl | H | O | CH—CH$_3$ | CH$_2$ |
| VIII | C—F | Cl | H | O | CH—CH$_3$ | CH$_2$ |
| IX | N | H | H | O | CH—OCH$_2$CH$_3$ | C(CH$_3$)$_2$ |
| X | N | Cl | H | O | CH—OCH$_2$CH$_3$ | C(CH$_3$)$_2$ |
| XI | N | Cl | H | O | CH—CH$_3$ | CH$_2$ |
| XII | N | H | H | O | CH$_2$ | O |
| XIII | N | H | H | N—CH$_3$ | C=O | C(CH$_3$)$_2$ |
| XIV | C—F | Cl | H | N—H | C=O | CH$_2$ |
| XV | N | H | H | N—CH$_3$ | C=O | C(CH$_3$)(CH$_2$CH$_3$) |
| XVI | N | H | H | N—CH$_2$CH$_3$ | C=O | C(CH$_3$)$_2$ |
| XVII | C—F | Cl | H | N—CH$_2$CH$_3$ | C=O | C(CH$_3$)$_2$ |
| XVIII | C—F | Cl | H | O | CH—COOCH$_3$ | C=O |

EXAMPLE VI–XVIII

Following the procedures described in the foregoing Examples I to V, the following Formula I compounds were also prepared:

VI The compound: 2-hydroxymethyl-5-(2-chloro-4-trifluoromethylphenoxy)-7-carbomethoxy-2,3-dihydrobenzofuran.

Although the invention has been illustrated by the foregoing Examples with regard to the preparation of certain compounds within the scope of Formula I, it is to be understood that other compounds within the scope of Formula I may readily be prepared by those skilled in the art simply by varying the choice of starting materials and using the same or similar techniques.

Weed control in accordance with this invention is affected by applying to the soil prior to emergence of weeds therefrom or to the plant surfaces subsequent to emergence from the soil, a herbicidally effective amount of a compound of this invention. It is, of course, to be understood that the term "a compound of this invention" also includes mixtures of such compounds or a formulation containing a compound or mixture of compounds of this invention.

The term "herbicidally effective amount" is that amount of a compound of this invention required to so injure or damage weeds such that the weeds are incapable of recovering following application while not causing substantial injury to any valuable crop amongst which the weeds might be growing. The quantity of compound of this invention applied in order to exhibit a satisfactory herbicidal effect may vary over a wide range and depends on a variety of factors, such as, for example, hardiness of a particular weed species, extent of weed infestation, climatic conditions, soil conditions, method of application, and the like. Typically, as little as one or less pound or acre of a compound of this invention would be expected to provide satisfactory weed control, although in some instances application rates in excess of one pound per acre, e.g., up to 2 or more pounds per acre might be required. Of course, the efficacy of a particular compound against a particular weed species may readily be determined by routine laboratory or field testing in a manner well known to the art. The compounds of the invention have exhibited herbicidal activity at an application rate as low as 0.025 pound per acre. It is expected that in most instances satisfactory weed control can be had at postemergence application rates in the range of 0.05 to 0.5 pound per acre and at preemergence application rates in the range of 0.1 to 1.0 pound per acre.

Of course, a compound of this invention can be formulated according to routine methods with any of several known and commonly used herbicidal diluents, adjuvants and carriers. The formulations can contain liquid carriers and adjuvants such as organic solvents, as well as emulsifiers, stabilizers, dispersants, suspending agents, spreaders, penetrants, wetting agents and the like. Typical carriers utilized in dry formulations include clay, talc, diatomaceous earth, silica and the like. Preferred formulations are those in the form of wettable powders, flowables, dispersible granulates or aqueous emulsifiable concentrates which can be diluted with water at the site of application. Also, dry formulations such as granules, dusts, and the like, may be used.

When desired, a compound of this invention can be applied in combination with other herbicidal agents to achieve even broader vegetative control. Typical herbicides, which can be conveniently combined with Formula I compound, include atrazine, hexazinone, metribuzin, ametryn, cyanazine, cyprazine, prometon, prometryn, propazine, simazine, terbutryn, propham, alachlor, acifluorfen, bentazon, metalachlor and N,N-dialkyl thiocarbamates such as EPTC, butylate or venolate. These, as well as other herbicides described, for example, in the *Herbicide Handbook of the Weed Science Society of America*, may be used in combination with a compound or compounds of the invention. Typically such formulations will contain from about 5 to about 95 percent by weight of a compound of this invention.

The herbicidal formulations contemplated herein can be applied by any of several methods known to the art. Generally, the formulation will be surfaced applied as an aqueous spray. Such application can be carried about by conventional ground equipment, or if desired, the sprays can be serially applied. Soil incorporation of such surface applied herbicides is accomplished by natural leaching, and is, of course, facilitated by natural rainfall and melting snow. If desired, however, the herbicides can be incorporated into the soil by conventional tillage means.

Compounds of this invention are believed effective for emergence of postemergence control of a wide variety of broadleaf and grassy weeds. Typical of the various species of vegetative growth that may be controlled, combated, or eliminated are, for example, annuals such as pigweed, lambsquarters, foxtail, crabgrass, wild mustard, field pennycress, ryegrass, goose grass, chickweed, wild oats, velvetleaf, purslane, barnyardgrass, smartweed, knotweed, cocklebur, kochia, medic, ragweed, hemp nettle, spurrey, pondweed, carpetweed, morningglory, ducksalad, cheatgrass, fall panicum, jimsonweed, witchgrass, watergrass, wild turnip, and similar annual grasses and weeds. Biennials that may be controlled include wild barley, campion, burdock, bull thistle, roundleaved mallow, purpose star thistle, and the like. Also controlled by the compounds of this invention are perennials such a quackgrass, Johnsongrass, Canada thistle, curley dock, field chickweed, dandelion, Russion knapweed aster, horsetail, ironweed, sesbania, cattail, wintercress, horsenettle, nutsedge, milkweed, sicklepod, and the like.

The compounds prepared as described in the Examples were individually tested for herbicidal efficacy against a variety of broadleaf and grassy weed species, under controlled laboratory conditions of light, humidity and temperature. Solvent solutions of said compounds were applied, both preemergence and postemergence, to test flats containing the various weed species, and herbicidal efficacy was evaluated vis a vis an untreated control, by periodic visual inspection after application of the compounds. Herbicidal efficacy was evaluated on a Numerical Injury Rating (NIR) scale of from 0 (no injury) to 10 (all plants dead). A NIR rating of 7–9 indicates sever injury; a NIR rating of 4–6 indicates moderate injury, i.e., plant growth is reduced to the extent that normal growth would be expected only under ideal conditions; and a NIR rating of 1–3 indicates slight injury.

The following table gives typical preemergence and postemergence NIR data for certain of the compounds of the foregoing Examples. Each compound was applied to each weed species at the indicated pound per acre rate and the NIR was determined about two weeks after application.

| Weed Species: | Compound of Example No. | | | | | | | |
|---|---|---|---|---|---|---|---|---|
| | III | | IV | | V | | XVII | |
| | Pre | Post | Pre | Post | Pre | Post | Pre | Post |
| Coffeeweed | 10 | 9 | 5 | 7 | 7 | 8 | 5 | 9 |
| Jimsonweed | 10 | 10 | 8 | 10 | 8 | 10 | 10 | 9 |
| Sicklepod | 9 | 9 | 2 | 0 | 3 | 5 | 1 | 2 |
| Lambsquarters | — | 8 | 9 | 5 | 9 | 9 | 10 | 8 |
| Teaweed | 10 | 10 | 8 | 8 | 8 | 10 | 8 | 8 |
| Velvetleaf | 10 | 10 | 8 | 10 | 8 | 9 | 7 | 10 |
| Morningglory | 6 | 10 | 1 | 8 | 6 | 9 | 3 | 8 |
| Yellow Foxtail | 10 | 10 | 8 | 8 | 5 | 1 | 5 | 8 |
| Johnsongrass | 10 | 10 | 5 | 7 | 7 | 5 | 7 | 7 |
| Wild Oats | 2 | 3 | 1 | 0 | 2 | 1 | 0 | 1 |
| Barn- | 10 | 8 | 2 | 3 | 2 | 3 | 1 | 7 |

| | Compound of Example No. | | | | | | | |
|---|---|---|---|---|---|---|---|---|
| | III | | IV | | V | | XVII | |
| Weed Species: | Pre | Post | Pre | Post | Pre | Post | Pre | Post |
| yardgrass | | | | | | | | |
| Rate, lb/A | 0.5 | 0.1 | 1.0 | 1.0 | 1.0 | 0.05 | 0.5 | 0.1 |

Although the invention has been illustrated in some detail by the foregoing, it is to be understood that many variations can be made therein by those skilled in the art without departing from the spirit and scope thereof as defined by the appended claims.

We claim:

1. A compound of the formula

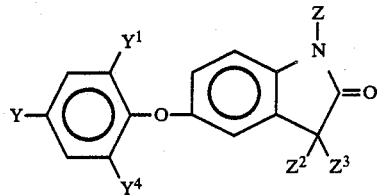

wherein:
Y, $Y^1$ and $Y^4$ are independently hydrogen, halogen, cyano, nitro or $C_1$ to $C_4$ alkyl substituted by up to three halogens; with the proviso that the group Y, $Y^1$ and $Y^4$ when taken together include no more than two cyano or nitro groups;
Z is $C_1$ to $C_4$ alkyl; $Z^2$ is hydrogen or $C_1$ to $C_6$ alkyl and $Z^3$ is hydrogen, $C_1$ to $C_6$ alkyl, $C_1$ to $C_6$ alkoxy, $C_1$ to $C_6$ alkoxyalkyl, $C_1$ to $C_6$ aminoalkyl, $C_1$ to $C_6$ hydroxyalkyl, $C_1$ to $C_6$ alkenyl or $C_1$ to $C_6$ alkynyl.

2. A compound of claim 1 wherein Y is trifluoromethyl; $Y^1$ is halogen; $Y^4$ is hydrogen or halogen; Z is $C_1$ to $C_4$ alkyl; and $Z^2$ and $Z^3$ are hydrogen or $C_1$ to $C_4$ alkyl.

3. A herbicidal composition containing an agronomically acceptable carrier and a herbicidally effective amount of a compound or mixture of compounds defined in claim 1.

4. In a method of controlling the growth of weeds wherein a herbicidally effective amount of herbicide is applied to the situs of the weeds wherein the improvement resides in using as the herbicide, a compound or mixture of compounds defined in claim 1.

* * * * *